United States Patent [19]

Taylor

[11] 4,227,293
[45] Oct. 14, 1980

[54] METHOD OF CATHETER MANUFACTURE

[75] Inventor: Glenn N. Taylor, Cary, Ill.

[73] Assignee: The Kendall Company, Boston, Mass.

[21] Appl. No.: 968,239

[22] Filed: Dec. 11, 1978

Related U.S. Application Data

[62] Division of Ser. No. 792,823, May 2, 1977, Pat. No. 4,147,169.

[51] Int. Cl.³ .............................................. B23P 11/02
[52] U.S. Cl. ........................................ 29/447; 264/230
[58] Field of Search ........................... 29/447; 264/230; 128/349 B

[56] References Cited

U.S. PATENT DOCUMENTS

| | | | |
|---|---|---|---|
| 3,640,282 | 2/1972 | Kamen | 128/349 B X |
| 3,714,316 | 1/1973 | Angeloff | 264/230 |
| 3,799,173 | 3/1974 | Kamen | 128/349 B X |
| 3,833,004 | 9/1974 | Vazquez | 264/230 X |
| 3,896,816 | 7/1975 | Mattler | 128/349 B |
| 3,932,926 | 1/1976 | Dotsko | 264/230 X |
| 4,035,454 | 7/1977 | Klein | 264/230 X |

Primary Examiner—Charlie T. Moon
Attorney, Agent, or Firm—Powell L. Sprunger

[57] ABSTRACT

A catheter having a flexible annular balloon secured on a shaft of the catheter by a pair of annular sleeves. A method is provided for securing the balloon to the shaft by shrinking the sleeves over grooves of the shaft.

3 Claims, 7 Drawing Figures

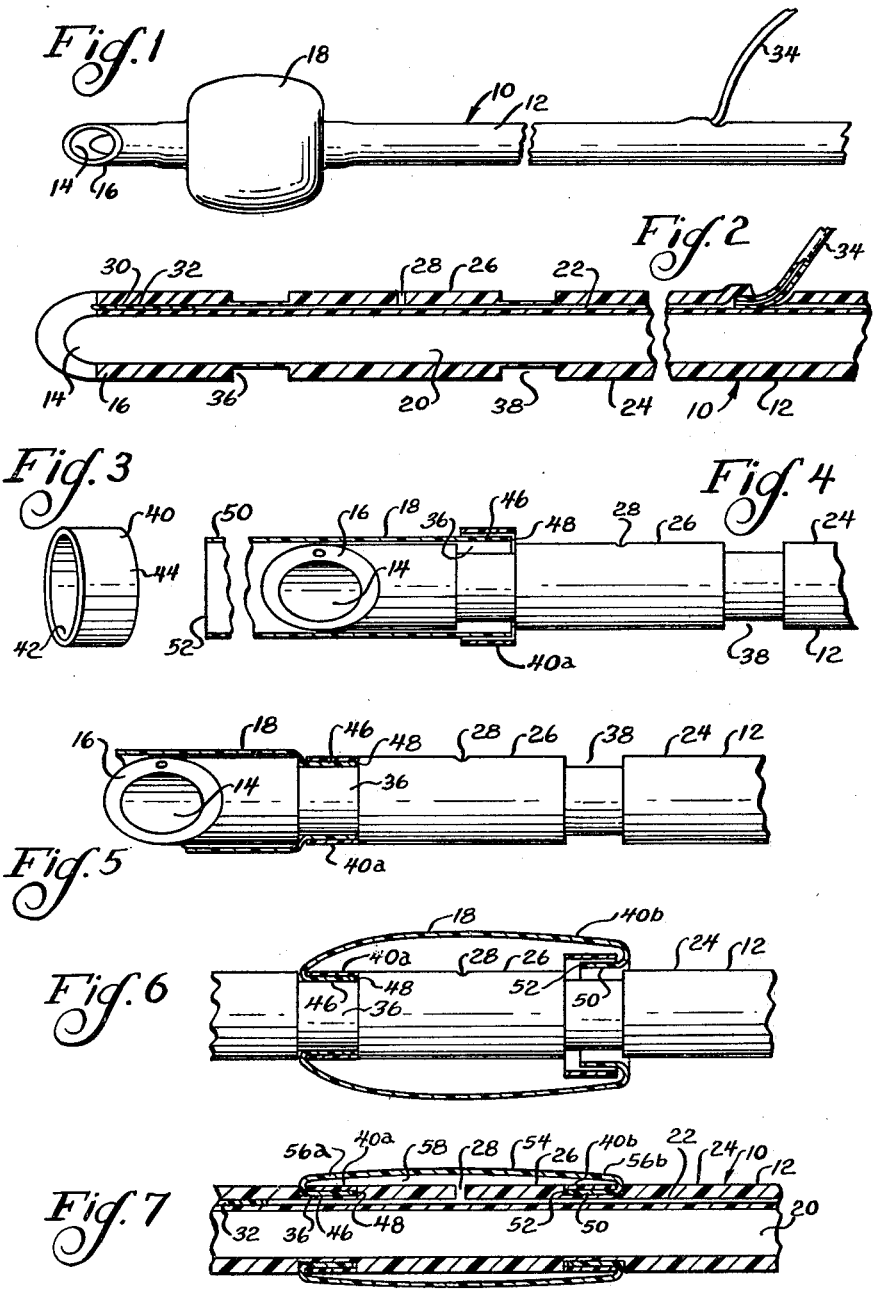

METHOD OF CATHETER MANUFACTURE

This is a division of Ser. No. 792,823, filed May 2, 1977, now U.S. Pat. No. 4,147,169, issued April 3, 1979.

SUMMARY OF THE INVENTION

The present invention relates to catheters and methods for fabricating such catheters.

A various assortment of catheters has been proposed for use on patients, such as endotracheal tubes and Foley catheters, in which the catheters have an inflatable balloon secured onto the catheter shafts. During use of the endotracheal tubes, the inflated balloons seal and retain the catheter in the patient's trachea, while the balloons of Foley or urinary catheters are inflated in the patient's bladder in order to retain the catheters in place.

The catheter balloons are made from a flexible material which is normally elastic, while the catheter shafts are preferably made from a more rigid material to permit easy placement and provide greater structural integrity of the shafts during use. Accordingly, in many cases it has become desirable to make the balloons and shafts from different materials, such as a silicone balloons for a non-silicone shaft, in order to achieve the desired characteristics required by the catheter balloons and shafts. In practice this has proven difficult to accomplish, since many of the dissimilar materials are not susceptible to conventional bonding techniques. Thus, the different materials frequently prove incompatible when attempts are made to attach the balloon to the shaft through use of heat sealing or known adhesives, and frequently a satisfactory bond cannot be obtained between the balloon and shaft in a conventional manner.

SUMMARY OF THE INVENTION

A principal feature of the present invention is the provision of an improved catheter and a method of fabricating the catheter in a simplified manner.

According to a method of the present invention a flexible annular balloon is secured on a shaft of the catheter by forming a pair of spaced annular grooves in an outer surface of the shaft, positioning a first end portion of the balloon intermediate a first shrinkable annular sleeve and one of the grooves, and shrinking the first sleeve to secure the first end portion of the balloon in the one groove. The remote end portion of the balloon is positioned intermediate a second shrinkable annular sleeve and the other of the grooves, and the second sleeve is shrunk to secure the remote end portion of the balloon in the other groove.

Thus, a feature of the present invention is that the balloon is attached to the shaft by shrinking the sleeves while securing end portions of the balloon in the grooves of the shaft.

Another feature of the present invention is that the balloon is secured on the shaft in a simplified manner.

Yet another feature of the invention is that the balloon may be secured to the shaft while obtaining an excellent bond between the balloon and shaft without the necessity of adhesives or sealing.

Still another feature of the invention is that the balloon may be readily secured to the shaft in spite that the balloon and shaft may be made from dissimilar materials which otherwise could not be bonded in a suitable manner.

A further feature of the invention is the provision of a catheter having a balloon secured to the catheter shaft in accordance with a method of the present invention.

Further features will become more fully apparent in the following description of the embodiments of this invention and from the appended claims.

DESCRIPTION OF THE DRAWINGS

In the drawings:

FIG. 1 is a fragmentary elevational view of a catheter of the present invention;

FIG. 2 is a fragmentary sectional view of an elongated shaft of the catheter of FIG. 1;

FIG. 3 is a perspective view of an annular sleeve utilized to secure an end portion of a balloon to the catheter shaft;

FIGS. 4–6 are fragmentary elevational views, taken partly in section, illustrating steps during securement of the balloon to the catheter shaft; and FIG. 7 is a fragmentary sectional view of the catheter illustrating the balloon as secured to the shaft according to a method of the present invention.

DESCRIPTION OF THE PREFERRED EMBODIMENTS

Referring now to FIG. 1, there is shown a catheter generally designated 10 having an elongated shaft 12, an opening 14 adjacent a distal end 16 of the shaft 12, and a balloon 18 of flexible material, such as silicone, secured to the shaft 12 in accordance with a method of the present invention. Although for convenience the catheter 10 is illustrated in the form of an endotracheal tube, it will be apparent that the principles of the present invention are equally applicable to other catheters, such as Foley or urinary catheters.

With reference to FIG. 2, the catheter shaft 12 has a main lumen 20 extending through the shaft and communicating with the opening 14 at the distal end 16 of the shaft 12. Also, the shaft 12 has an inflation lumen 22 in a wall 24 of the shaft 12 which communicates with an outer surface 26 of the shaft 12 through an aperture 28 in the wall 24. As shown, an outer end 30 of the inflation lumen 22 is blocked by a suitable plug 32, and the catheter 10 may have a tube or side arm 34 connected to the shaft 12 and defining an extension of the inflation lumen 22, such that fluid may be passed through the tube 34 and inflation lumen 22 to control inflation and deflation of the balloon 18 when secured to the shaft. The shaft 12 also has a pair of spaced first and second annular grooves 36 and 38 defining recesses in the outer surface 26 of the catheter shaft 12.

With reference to FIG. 3, the securing means comprises an annular sleeve 40 of shrinkable material having a bore 42 extending through a wall 44 of the sleeve 40. As will be seen below, first and second sleeves of similar structure are utilized to secure the balloon onto the catheter shaft, and for convenience the first and second sleeves will be designated by the reference numerals 40a and 40b during the following description. The sleeves 40a and 40b may be made of any suitable thermosetting or thermoplastic heat shrinkable material, such as polyethylene or polyvinyl chloride, in order that the sleeves shrink to a reduced size responsive to heating.

With reference to FIG. 4, the balloon 18 comprises an elongated annular sleeve of flexible material having a first end portion 46 defining a first end edge 48 of the balloon 18, and a second opposed end portion 50 defining a second end edge 52 of the balloon 18. As shown, prior to shrinking, the first sleeve 40a has an internal diameter greater than the outer diameter of the catheter shaft 12, and, in accordance with a method of the present invention, the first sleeve 40a is positioned over the location of the first groove 36 of the shaft. The first end portion 46 of the balloon 18 is positioned intermediate the first sleeve 40a and the first groove 36 with the first end edge 48 of the balloon 18 being directed toward the second groove 38, as shown.

Next, with reference to FIG. 5, the first sleeve 40a is subjected to a shrinking procedure, such as heat shrinking, such that the dimensions of the first sleeve 40a are significantly reduced and the first sleeve 40a snugly engages the first end portion 46 of the balloon 18 in the first groove 36. In this manner, the first end portion 46 of the balloon 18 is secured in the annular first groove 36 of the catheter shaft 12 by the shrunk sleeve 40a without the use of adhesives or heat sealing.

The remaining portion of the balloon 18 is then folded over the outer surface of the first sleeve 40a. As illustrated in FIG. 6, the enlarged second shrinkable sleeve 40b is positioned over the second groove 38, and the remote second end portion 50 of the balloon 18 is folded to a location intermediate the second sleeve 40b and second groove 83 with the second end edge 52 of the balloon being directed toward the first groove 36. The second sleeve 40b is then subjected to a shrinking treatment, such as heat shrinking, in order to reduce the dimensions of the second sleeve 40b, as shown in FIG. 7. As shown, the shrunk second sleeve 40b snugly engages against the second end portion 50 of the balloon 18 and secures the second end portion 50 of the balloon 18 in place intermediate the second sleeve 40b and the second groove 38.

Thus, the end portions 46 and 50 of the flexible balloon 18 are secured beneath the respective sleeves 40a and 40b in a simplified manner without the use of adhesives or sealing techniques. After fabrication, the first end edge 48 of the first balloon end portion 46 is directed toward the second groove 38 while the second end edge 52 of the second balloon end portion 50 is directed toward the first groove 36. As shown, a central portion 54 of the balloon extends over the outer surface 26 of the catheter shaft 12 with side portions 56a and 56b overlying outer surfaces of the respective shrunk first and second sleeves 40a and b. With reference to FIGS. 1 and 7, the balloon may be inflated at the time of use by passage of fluid through the tube 34, through the inflation lumen 22, and the wall aperture 28 into a cavity 58 defined intermediate the central portion 54 of the balloon 18 and the outer surface 26 of the catheter shaft 12. The balloon 18 may be deflated by reverse passge of fluid from the cavity 58 through the inflation lumen 22 and the tube 34.

The foregoing detailed description is given for clearness of understanding only, and no unnecessary limitations should be understood therefrom, as modifications will be obvious to those skilled in the art.

I claim:

1. A method of securing a flexible annular balloon on a catheter shaft, comprising the steps of:
    forming a pair of spaced annular grooves in an outer surface of the shaft;
    positioning a first end portion of the balloon intermediate a first shrinkable annular sleeve and one of said grooves in a configuration with an end edge of the first end portion directed toward the other of said grooves;
    shrinking said first sleeve over said first end portion to secure said first end portion of the balloon in said one groove;
    positioning the remote end portion of the balloon intermediate a second shrinkable annular sleeve and the other of said grooves in a configuration with an end edge of the remote end portion directed toward said one groove; and
    shrinking said second sleeve over said remote end portion to secure said remote end portion of the balloon in said other groove.

2. The method of claim 1 wherein said first and second sleeves are made from a heat shrinkable material, and the first and second shrinking steps comprise the steps of heat shrinking said first and second sleeves.

3. The method of claim 1 including the step of folding a remaining portion of said ballon over said first sleeve after the first shrinking step.

* * * * *